United States Patent [19]

Scott

[11] Patent Number: 5,227,548
[45] Date of Patent: Jul. 13, 1993

US005227548A

[54] OXYCHLORINATION OF ETHYLENE TO 1,2-DICHLOROETHANE

[75] Inventor: John D. Scott, Nr Northwich, England

[73] Assignee: Imperial Chemical Industries PLC, London, England

[21] Appl. No.: 641,862

[22] Filed: Jan. 16, 1991

Related U.S. Application Data

[62] Division of Ser. No. 449,771, Dec. 13, 1989, Pat. No. 5,011,808.

[30] Foreign Application Priority Data

Dec. 20, 1988 [GB] United Kingdom ................ 8829706

[51] Int. Cl.$^5$ .......................................... C07C 17/154
[52] U.S. Cl. .................................. 570/243; 570/244; 570/245
[58] Field of Search ................... 570/243, 244, 245

[56] References Cited

U.S. PATENT DOCUMENTS

| | | | |
|---|---|---|---|
| 3,624,170 | 11/1971 | Wakiyama et al. | 260/659 |
| 4,069,170 | 1/1978 | Blake | 260/659 |
| 4,123,467 | 10/1978 | Campbell et al. | 260/659 |
| 4,124,534 | 11/1978 | Leitert et al. | 252/441 |
| 4,910,354 | 3/1990 | Derleth et al. | 570/243 |

Primary Examiner—Marianne M. Cintins
Assistant Examiner—Kimberly J. Kestler
Attorney, Agent, or Firm—Cushman, Darby & Cushman

[57] ABSTRACT

A process for the oxychlorination of ethylene to 1,2-dichloroethane using an oxychlorination catalyst composition comprising a mixture of copper chloride, magnesium chloride and potassium chloride carried on a support therefor.

5 Claims, No Drawings

OXYCHLORINATION OF ETHYLENE TO 1,2-DICHLOROETHANE

This is a continuation of application No. 07/449,771, filed Dec. 13, 1989, now U.S. Pat. No. 5,011,808.

The present invention relates to an oxychlorination catalyst composition and to an oxychlorination process which uses such a catalyst composition.

The oxychlorination of ethylene to produce 1, 2-dichloroethane is a well-known process in the prior art. The process normally involves reacting ethylene with hydrogen chloride and an oxygen-containing gas (usually air or oxygen). The oxychlorination of ethylene is customarily performed in the presence of a catalyst comprising a copper compound, usually copper chloride ($CuCl_2$), deposited on a particulate support therefor. The catalyst composition, i.e., the catalyst itself and its support material, can be in the form of a fixed bed of particles or (as is now quite usual) a fluidised bed of particles during the reaction. The particulate support is frequently alumina, although other minerals such as silica gel, pumice clay, and diatomaceous earth have been suggested in the literature.

The use of copper chloride alone as the catalyst is known to be disadvantageous since this material is quite volatile at the oxychlorination reaction temperatures employed leading to a loss of catalyst activity over a period of time, particularly when the material is used in a fluidised bed reactor.

It is well known to improve the effectiveness of supported copper chloride in oxychlorination reactions by the addition of various alkali metal compounds, alkaline earth compounds and rare earth compounds (usually their chlorides) to the catalyst composition. Thus it has long been known to ameliorate the volatility problem of copper chloride by using it in conjunction with potassium chloride or sodium chloride. U.S. Pat. No. 4,069,170 discloses a supported oxychlorination catalyst (for use in fluidised-bed reactors) containing copper chloride in which the further problem of catalyst agglomeration or caking is avoided by the additional inclusion in the catalyst composition of didymium and lanthanum chlorides. U.S. Pat. No. 3,624,170 describes an oxychlorination catalyst composition consisting of copper chloride, sodium chloride and magnesium chloride (in specified ratios) on an inert porous carrier which is said to additionally overcome the problem of catalyst deactivation by contamination thereof by absorbed $Fe_2Cl_6$ when iron-type reactors (e.g. made of stainless steel) are employed for the oxychlorination process (as is quite usual). EP-A-0255156 describes an oxychlorination catalyst composition consisting of copper chloride, magnesium chloride. and sodium and/or lithium chloride (in specified ratios) deposited on alumina which is said to additionally overcome the corrosion effects suffered when using steel reactors for the oxychlorination process, caused by catalyst adherence and agglomeration on the reactor walls, and also to result in significantly improved catalyst activity and product yield.

We have now discovered a new and highly effective oxychlorination catalyst composition for the production of 1, 2 -dichloroethane from ethylene in which there is a synergistic contribution from at least two of its constituents.

According to the present invention there is provided an oxychlorination catalyst composition comprising a mixture of metallic chlorides carried on a support therefor, wherein said mixture of metallic chlorides consists essentially of a mixture of copper chloride, magnesium chloride, and potassium chloride.

There is also provided a process for the oxychlorination of ethylene to 1,2-dichloroethane (EDC) in which the oxychlorination reaction is performed using an oxychlorination catalyst composition comprising a mixture of metallic chlorides carried on a support therefor, wherein said mixture of metallic chlorides consists essentially of a mixture of copper chloride, magnesium chloride, and potassium chloride.

A metallic chloride(s) may be present in the catalyst composition of the invention ab initio (i.e. by employing the actual metallic chloride(s) for the preparation of the composition) or may be present as a result of employing a compound(s) which is (are) converted to the metallic chloride(s) under the reaction conditions of the oxychlorination process.

The metallic chlorides of the oxychlorination catalyst composition are preferably incorporated to provide amounts of Cu. Mg and K metals at the following levels (% by weight based on the weight of the total catalyst composition. i.e. including the support and the mixture of metallic chlorides):

Cu: 3 to 9%, more preferably 4 to 8%
Mg: 0.2 to 3%, more preferably 0.2 to 1.5%
K: 0.2 to 3% more preferably 0.5 to 2.0%

The metallic chlorides of the catalyst composition will preferably provide a Cu:Mg:K atomic ratio of 1:0.1–1,0:0.1–1.0, more preferably 1:0.2–0.9:0.2–0.9.

One of the most important features of the oxychlorination reaction is the selectivity of the EDC formation from ethylene, this being a measure of how much reacted ethylene has actually been converted to EDC rather than to by-products such as CO and $CO_2$. Selectivity to EDC formation tends to decrease with increasing conversion of ethylene (i.e. the % of ethylene undergoing reaction irrespective of what products are formed) and it is highly desirable to optimise this selectivity at any level of ethylene conversion. This is especially relevant opposite the growing use of ethylene recycle reactor systems in which unreacted ethylene is recycled to the reactor.

We have now discovered that in the oxychlorination catalyst composition of the invention which comprises a mixture of metallic chlorides consisting essentially of the three metallic chlorides as defined, the magnesium chloride ($MgCl_2$) and the potassium chloride (KCL) constituents thereof surprisingly act synergistically in the oxychlorination reaction to significantly improve the selectivity of the EDC formation from ethylene.

By "consisting essentially" we mean that the metallic chloride mixture either contains no other metallic chloride(s) apart from those specified (the usual case) or only contains other metallic chloride(s) in an amount which will have no tangible effect on the performance of the oxychlorination catalyst composition.

The merit of using potassium chloride as a burning suppression agent. i.e. a material which suppresses the "burning" of ethylene to form waste products (e.g. CO, $CO_2$) instead of the required EDC. is well established. Magnesium chloride has similar properties but is less effective. Surprisingly, the combined effect of the two constituents in the oxychlorination catalyst composition of the invention is superior to the effect achieved by presence of either in isolation. Moreover, such combination of the two constituents in the catalyst composition allows a high burning suppression without significantly decreasing the catalyst activity; this result would not be achieved by merely increasing the level of K ( in a composition containing no Mg) to achieve a comparably effective burn suppression as such a higher level of K would significantly decrease the level of catalyst activity Additionally, the oxychlorination catalyst composition of the invention has the further advantage of largely overcoming the catalyst fluidisation or stickiness problems associated with potassium-containing catalysts. Nor does the oxychlorination catalyst composition of the invention incur the deactivation or corrosion problems encountered when using steel reactors for the reaction process (see above).

The support material in the catalyst composition of the invention is preferably particulate alumina; the use of eta and/or gamma alumina is particularly preferred. The specific surface area of the support material (before metal chloride incorporation) is preferably in the range of from 20 to 400 $m^2g^{-1}$, more preferably 75 to 200 $m^2g^{-1}$. Standard support materials for oxychlorination catalysts have pore volume in the range of from 0.15 to 0.50 $cm^3g^{-1}$ and average particle size in the range of from 30 to 500 microns.

The method of preparation of the catalyst composition is not in itself critical. The simplest technique comprises impregnating the support in a single stage with an aqueous solution containing the required quantities of $CuCl_2$, $MgCl_2$, and KCl, the Cu and Mg chlorides conveniently being used as their hydrates for the dissolution. (Alternatively compounds may be used which convert to the metallic chlorides under the reaction conditions of the oxychlorination process). The aqueous solution is applied to the carrier and becomes absorbed; the impregnated support is then filtered if necessary and finally dried. Filtration will not be necessary if the support is contacted with a volume of the aqueous solution which is not more than sufficient to saturate the support.

It is to be understood that the copper and magnesium chlorides can exist either in an anhydrous state in the catalyst composition or, if desired, in the form of their hydrates; the latter situation will occur, for example, if the drying conditions employed when using an aqueous support impregnation technique are insufficient to drive off the water of crystallisation from the chlorides.

The oxychlorination reaction process of the invention can employ general techniques and general reaction conditions well established in the art. Thus ethylene may be brought into contact with HCl and molecular oxygen in the gas phase in the presence of the catalyst composition, which is preferably in a fluidised state (e.g. fluidising velocity in the range of from 1 to 100 cm $s^{-1}$) although fixed beds can also be used, at an elevated temperature (e.g. in the range of from 80° to 300° C., more usually 210° to 250° C.). The molecular oxygen may be introduced as such or in the form of an oxygen-containing gas mixture such as air. The ratio of the reactants used in the oxychlorination reaction is generally that used in prior art processes. Usually a slight excess of ethylene and a large excess of oxygen is employed relative to the amount of HCl. The pressure of the reaction is suitably in the range of from 1 to $2 \times 10^6$ $Nm^{-2}$ (1 to 20 bar), more usually $1 \times 10^5$ to $3 \times 10^5$ $Nm^{-2}$ (1 to 8 bar). The reactor material used is typically iron-based (usually a form of stainless steel) or nickel alloy-based, but glass may be employed for small-scale development work.

The present invention is now illustrated by reference to the following examples; the prefix C before an example denotes a comparative example. Unless otherwise specified, all parts, percentages, and ratios are on a weight basis.

EXAMPLES C1, C2, C3, C4, and 5

A sample a catalyst composition, corresponding to Example C1 was prepared as follows using an aqueous impregnation method. 18.78 g of $CuCl_2.2H_2O$ and 6.72 g of $MgCl_2.6H_2O$ were dissolved in 65 ml of water. The solution was added to 82 g of fluidisable gamma-type alumina support, to uniformly wet the support material. The wet solid was heated with stirring to produce a free flowing powder and dried for 2 hours at 150° C. in an oven. Approximately 100 g of finished catalyst were produced with a composition containing 7.0% Cu and 0.80% Mg based on the weight of the total catalyst composition (i.e. support plus metal chlorides), and the active phase on the support had a Cu:Mg atomic ratio of 1.0:0.3. The surface area of the support was 185 $m^2g^{-1}$ and gave a finished catalyst surface area of 120 $m^2g^{-1}$.

Samples (approximately 100 g) of catalyst compositions, corresponding to Examples C2, C3, C4 and 5, were prepared using the same technique described above using the appropriate amounts and types of metal chlorides (see following table) The catalyst compositions had the following metal contents.

| Ex. No. | Metal Contents of Composition %* | | | | Atomic Ratios in Composition | | | |
|---|---|---|---|---|---|---|---|---|
| | Cu | Mg | Na | K | Cu | Mg | Na | K |
| C1 | 7.0 | 0.80 | — | — | 1.00 | 0.30 | — | — |
| C2 | 7.0 | — | 0.76 | — | 1.00 | — | 0.30 | — |
| C3 | 7.0 | 0.40 | 0.38 | — | 1.00 | 0.15 | 0.15 | — |
| C4 | 7.0 | — | — | 1.29 | 1.00 | — | — | 0.30 |
| 5 | 7.0 | 0.40 | — | 0.645 | 1.00 | 0.15 | — | 0.15 |

*% w/w based on the finished catalyst composition.

EXAMPLES C6, C7, C8, C9 and 10

The oxychlorination catalysts of the preceding examples were each tested in a glass fluidised bed micro-reactor, fed with ethylene, air and HCl and controlled at 245° C. (reaction temperature). The reactor was operated at atmospheric pressure to give a gas superficial linear velocity of 1.0 cm $s^{-1}$ and a 7 second gas contact time with the catalyst. The reactor vent was diluted with nitrogen to avoid condensation and passed through a water scrubber. The products formed were analysed using chromatography and the unreacted HCl was calculated from measurements of the acidity of the vented scrubber water. Using premixed gases with a fixed $C_2H_4:O_2$ feed ratio of approximately 1.7:1. the $C_2H_4:HCl$ feed ratio was adjusted to adhieve a 98% HCl conversion.

In particular, the "ethylene burn" in each run was determined, i.e. the % of reacted ethylene that had been converted to CO plus $CO_2$; the proportion of EDC formed was also determined. The following results were obtained.

| Ex. No. | Source of Catalyst Composition | Feed Ratio $C_2H_4:HCl:O_2$ | % HCl Feed Conversion | % Ethylene Reaction Selectivity | |
|---|---|---|---|---|---|
| | | | | Burning $CO + CO_2$ | EDC |
| C6 | Ex C1 (Cu/Mg) | 1.09:2.0:0.65 | 98.0 | 5.5 | 93.9 |
| C7 | Ex C2 (Cu/Na) | 1.26:2.0:0.78 | 97.9 | 7.7 | 92.1 |
| C8 | Ex C3 (Cu/Mg/Na) | 1.19:2.0:0.70 | 98.0 | 6.4 | 93.4 |
| C9 | Ex C4 (Cu/K) | 1.19:2.0:0.70 | 98.0 | 5.6 | 94.1 |
| 10 | Ex 5 (Cu/Mg/K) | 1.11:2.0:0.66 | 98.0 | 4.9 | 94.9 |

It can be deduced from a comparison of the results that magnesium and potassium have a synergistic effect in the invention catalyst composition in reducing the ethylene burning reaction and thus increasing the ethylene to EDC reaction selectivity. There is no comparable enhancement in performance of the Cu/Na/Mg formula when compared with the Cu/Mg formula and the performance of the sodium-based catalysts were inferior to the Cu/Mg/K catalysts.

EXAMPLES C11, C12, and 13

A second set of catalyst compositions corresponding to Examples C10, C11 and C12 was prepared containing higher Mg and K additive levels. The impregnation technique employed was as described supra, and the compositions had the following metal contents.

| Ex. No. | Metal Content of Composition %* | | | | Atomic Ratios in Composition | | | |
|---|---|---|---|---|---|---|---|---|
| | Cu | Mg | Na | K | Cu | Mg | Na | K |
| C11 | 7.0 | 1.60 | — | — | 1.00 | 0.60 | — | — |
| C12 | 7.0 | — | — | 2.58 | 1.00 | — | — | 0.60 |
| 13 | 7.0 | 0.80 | — | 1.29 | 1.00 | 0.30 | — | 0.30 |

*% w/w based on the finished catalyst composition.

EXAMPLES C14, C15 and 16

The oxychlorination catalyst compositions of Examples C11, C12 and 13 were similarly tested in order to demonstrate the syngergistic effect at higher Mg and K additive levels. In this study, a $C_2H_4:O_2$ ratio of approximately 1.4 was employed with the $C_2H_4:HCl:O_2$ feed ratio in each case being 1.01:2.00:0.75.

| Ex. No. | Source of Catalyst Composition | Feed Ratio $C_2H_4:HCl:O_2$ | % HCl Feed Conversion | % Ethylene Reaction Selectivity | |
|---|---|---|---|---|---|
| | | | | Burning $CO + CO_2$ | EDC |
| C14 | Ex C11 (Cu/Mg) | 1.01:2.00:0.75 | 98.0 | 2.9 | 96.2 |
| C15 | Ex C12 (Cu/K) | 1.01:2.00:0.75 | 98.1 | 3.6 | 95.9 |
| 16 | Ex C13 (Cu/Mg/K) | 1.01:2.00:0.75 | 98.0 | 2.6 | 96.7 |

I claim:
1. Process for the oxychlorination of ethylene to 1,2-dichloroethane in which the oxychlorination reaction is performed using an oxychlorination catalyst composition comprising a mixture of metallic chlorides carried on a support therefor, wherein said mixture of metallic chlorides consists essentially of a mixture of copper chloride, magnesium chloride, and potassium chloride, and wherein the copper is present in an amount of 3 to 9%, the magnesium is present in an amount of 0.2 to 3% and the potassium is present in an amount of 0.2 to 3% by weight based on the weight of the catalyst composition.

2. Process according to claim 1 wherein the oxychlorination catalyst composition contains 0.1 to 1 atoms of magnesium, and 0.1 to 1 atoms of potassium per atom of copper.

3. Process according to claim 1 wherein the support material of the oxychlorination catalyst composition employed in the process is particulate alumina.

4. Process according to claim 3 wherein the alumina of the catalyst composition used in the process is eta and/or gamma alumina.

5. Process according to claim 1 wherein the catalyst composition is employed as a fluidised bed or a fixed bed of particles.

* * * * *